US012774260B2

(12) United States Patent
Haag et al.

(10) Patent No.: US 12,774,260 B2
(45) Date of Patent: Oct. 27, 2026

(54) PROCESS FOR PRODUCING OLEFINS FROM OXYGENATES WITH VARIABLE PRODUCTION OF ETHYLENE AND PROPYLENE

(71) Applicant: AXENS, Rueil-Malmaison (FR)

(72) Inventors: Stephane Haag, Frankfurt am Main (DE); Martin Gorny, Eschborn (DE); Bryce Williams, Frankfurt am Main (DE); Thomas Renner, Frankfurt am Main (DE)

(73) Assignee: AXENS, Rueil-Malmaison (FR)

( * ) Notice: Subject to any disclaimer, the term of this patent is extended or adjusted under 35 U.S.C. 154(b) by 317 days.

(21) Appl. No.: 18/387,651

(22) Filed: Nov. 7, 2023

(65) Prior Publication Data

US 2024/0150259 A1 May 9, 2024

(30) Foreign Application Priority Data

Nov. 9, 2022 (EP) .................................... 22206313

(51) Int. Cl.

| | |
|---|---|
| ***C07C 1/20*** | (2006.01) |
| ***C07C 7/00*** | (2006.01) |
| ***C07C 7/04*** | (2006.01) |
| ***C07C 11/04*** | (2006.01) |
| ***C07C 11/06*** | (2006.01) |

(52) U.S. Cl.

CPC .................. *C07C 1/20* (2013.01); *C07C 7/00* (2013.01); *C07C 11/04* (2013.01); *C07C 11/06* (2013.01)

(58) Field of Classification Search

CPC .... C07C 1/20; C07C 1/24; C07C 7/00; C07C 7/04; C07C 11/04; C07C 11/06; Y02P 30/20; Y02P 30/40; C10G 3/42

See application file for complete search history.

(56) References Cited

U.S. PATENT DOCUMENTS

| | | | |
|---|---|---|---|
| 2014/0187836 | A1 | 7/2014 | Sadasivan Vijayakumari et al. |
| 2016/0068452 | A1 | 3/2016 | Rothamel et al. |
| 2017/0362141 | A1 | 12/2017 | Castillo-Welter et al. |

FOREIGN PATENT DOCUMENTS

| | | |
|---|---|---|
| CN | 103 694 072 | 4/2016 |
| DE | 10 2014 112792 | 3/2016 |

OTHER PUBLICATIONS

European Search Report for corresponding EP 22206313.3, Apr. 26, 2023.

*Primary Examiner* — Youngsul Jeong
*Assistant Examiner* — Jason Y Chong
(74) *Attorney, Agent, or Firm* — Csaba Henter; MILLEN, WHITE, ZELANO & BRANIGAN, P.C.

(57) ABSTRACT

The invention relates to a process for producing olefins from oxygenates with variable production of ethylene and propylene. According to the invention, the process is switched from a state 1 with lower ethylene production to a state 2 with higher ethylene production in that:

the fraction C2re of the ethylene product stream which is recycled to the OTO reactor is lowered from a first value C2re,1 to a second value C2re,2, resulting in a change dC2re=C2re,1−C2re,2, the fraction C4+re of the C4+ product stream containing C4+ olefins which is recycled to the OTO reactor is lowered from a first value C4+re,1 to a second value C4+re,2, resulting in a change dC4+re=C4+re,2−C4+re,1, where the changes dC2re and dC4+re in a mass flow ratio dC4+re/dC2re, where the mass flow ratio is between 70% and 130%.

17 Claims, 1 Drawing Sheet

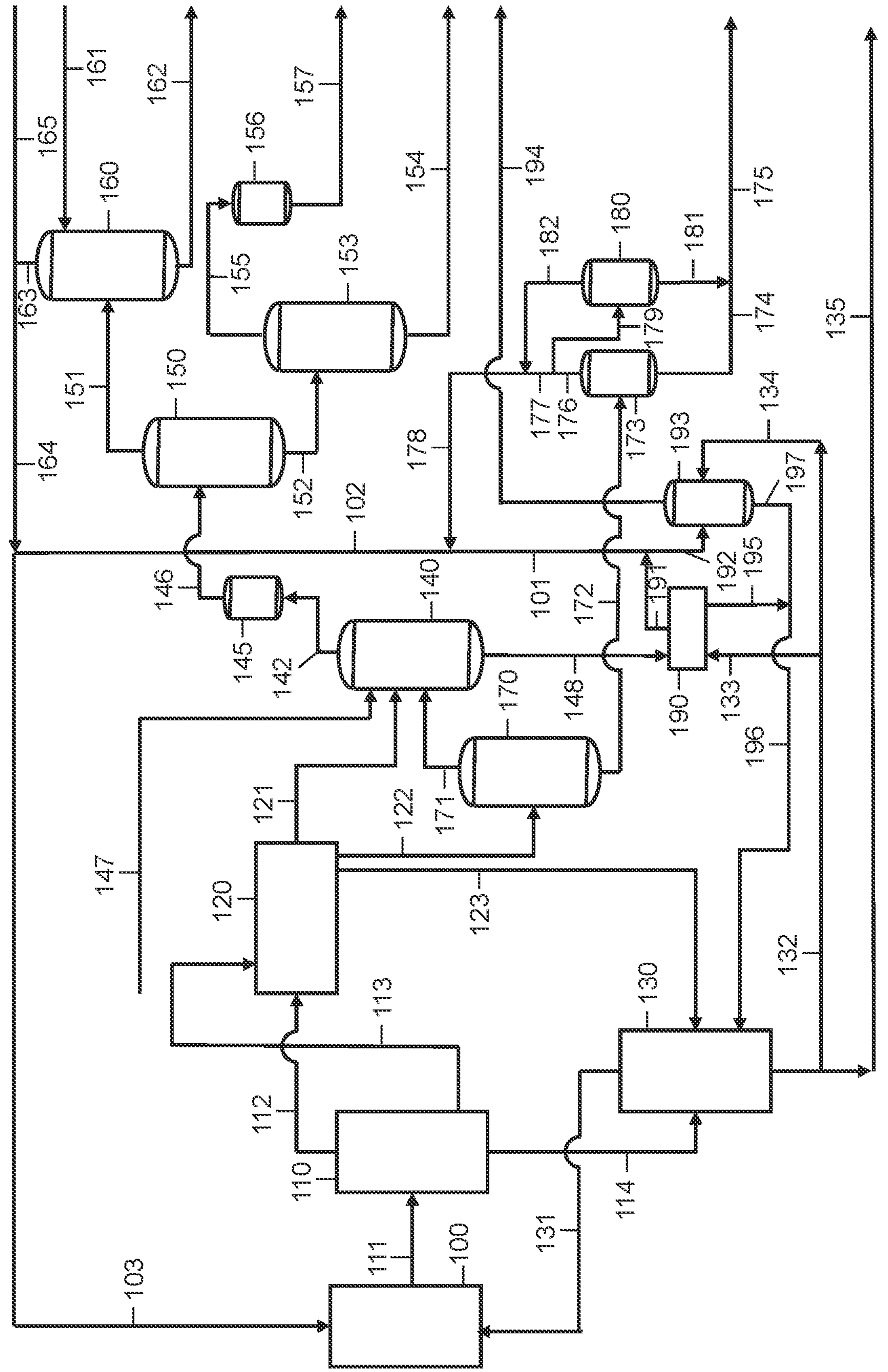
100
101
102
103
110
111
112
113
114
120
121
122
123
130
131
132
133
134
135
140
142
145
146
147
148
150
151
152
153
154
155
156
157
160
161
162
163
164
165
170
171
172
173
174
175
176
177
178
179
180
181
182
190
191
192
193
194
195
196
197

PROCESS FOR PRODUCING OLEFINS FROM OXYGENATES WITH VARIABLE PRODUCTION OF ETHYLENE AND PROPYLENE

CROSS REFERENCE TO RELATED APPLICATIONS

This application claims the benefit of priority under 35 U.S.C. § 119 (a) and (b) to European Patent Application No. 22206313.3, filed Nov. 9, 2022, the entire contents of which are incorporated herein by reference.

BACKGROUND

Field of the Invention

The invention relates to a process for producing olefins from oxygenates (OTO) with variable production of ethylene and propylene. In particular, the invention relates to a configuration of a specific OTO process which permits production of ethylene and propylene with variable proportions in the overall product, in order to use these short-chain olefins as monomers as feedstock in a downstream polymerization, for example a copolymerization of ethylene and propylene, especially a generation of polypropylenes (PP) with ethylene as copolymer component.

Prior Art

Short-chain olefins, for example propylene (propene) and ethylene (ethene), are among the most important commodities in the chemical industry. The reason for this is that, proceeding from these unsaturated compounds with a short chain length, it is possible to form molecules having a long-chain carbon skeleton and additional functionalizations. These short-chain olefins find wide use particularly in the production of plastics by polymerization.

The main source of short-chain olefins in the past was steamcracking, i.e. thermal cracking in mineral oil processing. In the past few years, however, further processes for preparing short-chain olefins have been developed. One reason for this is rising demand that can no longer be covered by the available sources, secondly, the increasing scarcity of fossil raw materials is requiring the use of different starting materials.

What are called the MTP (methanol-to-propylene) or else MTO (methanol-to-olefin) processes for producing propylene and other short-chain olefins proceed from methanol as starting material. By way of generalization, reference is also made in this context to oxygenate-to-olefin (OTO) processes, since oxygen-containing organic components such as methanol or dimethyl ether (DME) are also referred to as oxygenates. In these heterogeneously catalysed processes, accordingly, there is at first partial formation of the dimethyl ether intermediate from methanol for example, and subsequently of a mixture of ethylene and propylene and hydrocarbons having a higher molar mass, including olefins, from a mixture of methanol and dimethyl ether. Moreover, water is present in the product stream, which firstly originates from the process steam which is optionally supplied to the MTO reactor for modulation of reaction and secondly from the water of reaction produced in the MTP reactor, which is formed as a coproduct of the olefin formation reaction.

The subsequent purification is intended firstly to remove unwanted by-products and unconverted reactants, and to prepare the individual hydrocarbon fractions with maximum purity. Typically, for this purpose, a quench system is employed in the first step. Quenching is understood to mean an abrupt or shock cooling which is usually brought about by direct heat exchange with a fluid quench medium. If a liquid such as water or methanol is used for the purpose, there is additionally a certain cleaning effect in relation to the remaining gas phase.

One example of the purification that follows an OTO reaction can be found in patent publication DE 10 2014 112 792 A1, which describes how, in a first step, a heterogeneously catalysed conversion of at least one oxygenate to a product stream comprising C2 olefins, C3 olefins, C4 olefins, C5/6 hydrocarbon compounds and C7+ hydrocarbon compounds and, in a second step, a removal of a propylene stream consisting to an extent of at least 95% by weight of C3 olefins is generated.

The further purification units that are described in DE 10 2014 112 792 A1 are in accordance with the concept customary in the art. The quenching may already bring about a coarse separation of the fractions according to their chain length of the resultant olefins due to partial condensation, thus allowing a liquid C4+ fraction to be discharged from the quench. The C4− fraction separated in gaseous form is subsequently introduced into a compression stage. The C4− fraction from the compression is then sent to a separation apparatus in which C3− hydrocarbons are separated from the C4+ hydrocarbons. In subsequent purifying steps the C3 fraction is separated from the C2− fraction in a further separating unit, wherein this has to be carried out under pressure owing to the low boiling points of the two fractions. Overall, the purification of the product stream is complicated since the aim is a high purity of the products. This is true of MTP plants having typical production capacities of about 470 kta of propylene, but becomes even more crucial if the plant capacity is lower (100 kta or 200 kta of propylene). This means that small plants are relatively uneconomic.

In particular, the products of the MTP process include a propylene product stream, and ethylene product stream and a gasoline fraction, the latter comprising higher paraffins, olefins, aromatics and cyclic hydrocarbons. Moreover, various hydrocarbons are obtained within the process, in particular streams containing C4 olefins, C5 olefins and C6+ olefins, which are recycled predominantly or completely to the MTP reactor, where they are cleaved to short-chain olefins, which improves the yield of the propylene and ethylene target products.

The main aim of the MTP process in its existing configuration is the maximization of the yield of propylene, which is a particularly sought-after product. However, there is also a need to provide ethylene and propylene, ideally with variable proportions, for a copolymerization of the two olefins. For this purpose, the configurations of the MTP process and of other OTO processes that are known from the prior art do not offer a satisfactory solution to date.

SUMMARY

It is therefore an object of the present invention to propose a process for producing olefins from oxygenates with variable production of ethylene and propylene, which avoids the disadvantages of OTO processes mentioned that are known to date from the prior art.

Oxygenates are in principle to be understood to mean all oxygen-containing hydrocarbon compounds that can be converted under oxygenate conversion conditions to olefins, especially to short-chain olefins such as propylene, and further hydrocarbon products.

The oxygenate conversion conditions required for the conversion of oxygenates to olefin products are known to the person skilled in the art from the prior art, for example the publications discussed in the introduction. These are those physicochemical conditions under which a measurable conversion, preferably one of industrial relevance, of oxygenates to olefins is achieved. Necessary adjustments of these conditions to the respective operational requirements will be made by those skilled in the art on the basis of routine experiments. Any specific reaction conditions disclosed may serve here as a guide, but they should not be regarded as limiting in relation to the scope of the invention.

Thermal separation processes for the purposes of the present invention include all separation processes based on the establishment of a thermodynamic phase equilibrium. Distillation or rectification are preferred. In principle, however, the use of other thermal separation processes is also conceivable, for example of extraction or extractive distillation.

A process for producing olefins with variable production of ethylene and propylene is understood to mean that the mass ratio of the ethylene and propylene target products is varied in an intentional and reproducible manner by the inventive changes in process conditions.

The distinction between a first state 1 with lower ethylene production and a second state 2 with higher ethylene production should be regarded as being purely qualitative and is based on relative changes in the mass flow of ethylene discharged from the process as target product.

The statement that the lowering of the fraction C2re and the increasing of at least one fraction selected from the group comprising: C4+re, C4re, C5re, C6+re, are subsequently reversed in order to move the process from a second state 2 with higher ethylene production back to a first state 1 with lower ethylene production should be understood such that first a change in the process implementation from state 1 into state 2 has been undertaken, and the process has then been moved back from state 2 into state 1 by completely or partly reversing the changes.

The statement that steady-state operation of the overall process and of the individual process stages is assured should be considered on the basis of the overall process to mean that, for a defined set of process conditions within a certain period of time, a state in which constant mass flow rates of the ethylene and propylene target products are discharged from the process over a prolonged period of time or period of operation of the process according to the invention is attained. Based on individual process stages, this should likewise be understood to mean that, for the process stage under consideration, a steady state is attained and, for example, overfilling and emptying of separation columns is avoided. The period of operation here is the duration over which the processes operated and the processed products are produced. A customary unit for this parameter is hours on stream (h or hos).

If it is stated that a stream comprises hydrocarbons and comprises specifically olefins, this is understood to mean that the olefins are a specific subgroup of the hydrocarbons and that, accordingly, other non-olefinic hydrocarbons may be present in the stream.

Short-chain olefins in the context of the present invention are especially understood to mean olefins that are gaseous under ambient conditions, for example ethylene, propylene and the isomeric butenes 1-butene, cis-2-butene, trans-2-butene, isobutene.

Higher hydrocarbons in the context of the present invention are especially understood to mean hydrocarbons that are liquid under ambient conditions.

Hydrocarbon fractions are identified using the following nomenclature: "Cn fraction" refers to a hydrocarbon fraction containing predominantly hydrocarbons of carbon chain length n, i.e. having n carbon atoms. "Cn− fraction" refers to a hydrocarbon fraction containing predominantly hydrocarbons of carbon chain length n but also containing shorter carbon chain lengths. "Cn+ fraction" refers to a hydrocarbon fraction containing predominantly hydrocarbons of carbon chain length n but also containing longer carbon chain lengths. Owing to the physical separation processes used, for example distillation, separation in terms of carbon chain length should not be considered to mean that hydrocarbons having another chain length are rigorously excluded. For instance, a Cn− fraction, depending on the process conditions of the separation process, will still contain small amounts of hydrocarbons having a carbon number greater than n.

The solid, liquid and gaseous/vaporous states of matter mentioned should always be considered in relation to the local physical conditions that exist in the respective process step or in the respective plant component, unless stated otherwise. In the context of the present patent application, the gaseous and vapor states of matter should be considered to be synonymous.

In the context of the present invention, a division or separation/removal of a stream of matter is understood to mean production of at least two substreams from the original stream of batter, where separation/removal is associated with an intentional alteration of the physical composition of the substreams obtained relative to the original stream of matter, for example by application of a thermal separation process or at least thermal separation step to the original stream of matter. By contrast, division of the original stream of matter is generally not associated with any change in the physical composition of the substreams obtained.

A gasoline fraction is understood to mean a substance mixture which is in liquid form under ambient conditions, consists predominantly, preferably substantially completely, of higher hydrocarbons and may be suitable for use as a gasoline fuel. A corresponding stream of matter is referred to as gasoline product stream.

The predominant part of a fraction, of a stream of matter, etc. is understood to mean a proportion quantitatively greater than each of the other proportions on their own. Especially in the case of binary mixtures or in the case of separating of a fraction into two portions, this is understood to mean a proportion of more than 50% by weight, unless stated otherwise in the specific case.

The statement that a stream of matter consists predominantly of one component or group of components is understood to mean that the molar proportion (mole fraction) or proportion by mass (mass fraction) of this component or component group is quantitatively greater than each of the other proportions of other components or component groups in the stream of matter on their own. Especially in the case of binary mixtures, this is understood to mean a proportion of more than 50%. Unless stated otherwise in the specific case, the basis used here is the proportion by mass (mass fraction).

Ethylene production or propylene production is understood to mean the amount of ethylene or propylene produced per unit time. A customary unit is tonnes per day (t/d).

According to the invention, the process is switched from a state 1 with lower ethylene production to a state 2 with higher ethylene production in that:

the fraction C2re of the ethylene product stream which is recycled to the OTO reactor is lowered from a first value C2re,1 to a second value C2re,2, resulting in a change dC2re=C2re,1−C2re,2, the fraction C4+re of the C4+ product stream containing C4+ olefins which is recycled to the OTO reactor is lowered from a first value C4+re,1 to a second value C4+re,2, resulting in a change dC4+re=C4+re,2−C4+re,1, where the changes dC2re and dC4+re in a mass flow ratio dC4+re/dC2re, where the mass flow ratio is between 70% and 130%, preferably between 80% and 120%, further preferably between 90% and 110%, most preferably 100%.

Surprisingly, the inventive changeover in the process implementation from state 1 with lower ethylene production to a state 2 with higher ethylene production does not lead to a loss of the valuable propylene target product; instead, there is a decrease in the yield for the gasoline product containing C4+ paraffins and aromatics, which has a much lower value.

Overall, the advantages associated with the invention can be summarized as follows:

The production of the valuable light, short-chain olefins, especially of ethylene and propylene, is increased.

The process can provide product streams with different ethylene and propylene content as monomers for a subsequent copolymerization.

The filling of any ethylene storage tanks required is better controlled and better matched to the needs of any downstream copolymerization.

The result is more stable process implementation.

A second aspect of the invention is characterized in that the movement of the process from a first state 1 with lower ethylene production to a second state 2 with higher ethylene production reduces propylene production only by a maximum of 5%, preferably only by a maximum of 3%. The values achieved for ethylene production and propylene production are dependent on the state of conditioning of the OTO catalyst, which is complete, for example, at 1000 hours on stream. The result is then a period of operation referred to as "middle of run" (MOR) in which, in state 2, a constantly high level of propylene production, or one reduced by a maximum of 5%, preferably only by a maximum of 3%, with simultaneously increased ethylene production compared to state 1 is observed.

A third aspect of the invention is characterized in that the movement of the process from a first state 1 with lower ethylene production to a second state 2 with higher ethylene production reduces the sum total (ethylene production+propylene production) by at least 8%, preferably by at least 10%. The values achieved for ethylene production and propylene production are dependent on the state of conditioning of the OTO catalyst, which is complete, for example, at 1000 hours on stream. The result is then a period of operation referred to as "middle of run" (MOR) in which, in state 2, the sum total (ethylene production+ propylene production) can be increased by at least 8%, preferably by at least 10%. A slight decrease in propylene production is more than compensated for here by the increase in ethylene production. In one example, propylene production is reduced only by a maximum of 5%, preferably only by a maximum of 3%.

A fourth aspect of the invention is characterized in that the process is moved from a first state 1 with lower ethylene production to a second state 2 with higher ethylene production after no earlier than 600 hours on stream, preferably after no earlier than 800 hours on stream, most preferably after no earlier than 1000 hours on stream, of the OTO catalyst. Studies show that, beyond the period of time mentioned, a significant decrease in propylene production is no longer expected when the process is moved from state 1 to state 2. Beyond the periods of time mentioned, in state 2, a constantly high level of propylene production corresponding to state 1 is observed with simultaneously elevated ethylene production compared to state 1.

A fifth aspect of the invention is characterized in that the process is moved from a first state 1 with lower ethylene production to a second state 2 with higher ethylene production after no later than 200 hours on stream, preferably after no later than 100 hours on stream, most preferably after no later than 50 hours on stream, of the OTO catalyst. In this aspect of the invention, although there is a temporary reduction in propylene production, this shortens the forming phase or conditioning phase, i.e. that period of time after which constant reaction characteristics of the OTO catalyst are observed ("middle of run", MOR), before—at very long operating times in the "end of run" (EOR) period of operation at typically more than 7000 hos—ageing effects of the OTO catalyst occur. Beyond the "middle of run" (MOR) period of operation, in state 2, a constantly high level of propylene production corresponding to state 1 is observed with simultaneously elevated ethylene production compared to state 1.

A sixth aspect of the invention is characterized in that the C4+ product stream containing C4+ olefins is separated further by thermal separation methods into at least one further olefin product stream selected from the group comprising:

(c31) a C4 olefin product stream comprising butenes which is at least partly recycled in a fraction C4re to the OTO reactor, where the recycled fraction C4re is increased from a first value C4re,1 to a second value C4re,2, resulting in a change dC4re=C4re,2−C4re,1, (c32) a C5 olefin product stream comprising pentenes which is at least partly recycled in a fraction C5re to the OTO reactor, where the recycled fraction C5re is increased from a first value C5re,1 to a second value C5re,2, resulting in a change dC5re=C5re,2−C5re,1, (c33) a C6+ olefin product stream comprising hexenes and optionally olefins having more than six carbon atoms which is at least partly recycled in a fraction C6+re to the OTO reactor, where the recycled fraction C6+re is increased from a first value C6+re,1 to a second value C6+re,2, resulting in a change dC6+re=C6+re,2−C6+re,1, where the change dC4+re is calculated as the sum total of the changes dC4re+dC5re+dC6+re.

What is advantageous here is the high flexibility of the process obtained thereby, since multiple product streams (c31), (c32), (c33) are available individually or in combination for compensation of the reduction in the fraction C2re of the product stream which is recycled to the OTO reactor.

A seventh aspect of the invention is characterized in that, from the group of further olefin product streams, only the C4 olefin product stream is recycled at least partly in a fraction C4re to the OTO reactor. This has the advantage that a less sought-after product compared to other olefins, namely C4 olefins, is thus converted to a higher degree to the sought-after olefins ethylene and propylene.

An eighth aspect of the invention is characterized in that, from the group of further olefin product streams, only the C5 olefin product stream is recycled at least partly in a fraction C5re to the OTO reactor. This has the advantage that, for stoichiometric reasons, the catalytic cleavage of the C5 olefins that have been recycled to enhance degree improves both the yield of ethylene and the yield of propylene.

A ninth aspect of the invention is characterized in that, from the group of further olefin product streams, only the C6+ olefin product stream is recycled at least partly in a fraction C6+re to the OTO reactor. This has the advantage that C6+ olefins obtained, which have higher reactivity for the catalytic cleavage to give ethylene and propylene by comparison with shorter-chain olefins, can be utilized to an increased degree for the production of these target products. Furthermore, this stream contains further reactive compounds, for example cycloparaffins (saturated naphthenes) and cycloolefins (unsaturated naphthenes) but can likewise react to give ethylene and propylene, as studies have shown.

A tenth aspect of the invention is characterized in that, from the group of further olefin product streams, two of these streams are recycled at least partly to the OTO reactor. In one example, the C4 olefin product stream and the C5 olefin product stream are recycled at least partly to the OTO reactor. In one example, the C4 olefin product stream and the C6+ olefin product stream are recycled at least partly to the OTO reactor. In one example, the C5 olefin product stream and the C6+ olefin product stream are recycled at least partly to the OTO reactor. The configurations according to the examples described have the advantage of elevated flexibility of the process implementation.

An eleventh aspect of the invention is characterized in that all other olefin product streams are recycled at least partly to the OTO reactor. This has the advantage of elevated production of the ethylene and propylene target products, while there is a reduction in energy expenditure for the separation and purification of the further olefin product streams. Moreover, the individual process stages are more uniformly loaded, and a new steady state 2 is attained more quickly.

A twelfth aspect of the invention is characterized in that the lowering of the fraction C2re and the increasing of at least one fraction selected from the group comprising: C4+re, C4re, C5re, C6+re, are effected such that the ethylene/propylene product ratio is between 1% and 20% by weight, preferably between 2% and 20% by weight. Studies show that ethylene/propylene product ratios within the range of values mentioned can be processed in a particularly efficient and flexible manner in an ethylene/propylene copolymerization for production of polypropylene with ethylene as comonomer.

A thirteenth aspect of the invention is characterized in that the lowering of the fraction C2re and the increasing of at least one fraction selected from the group comprising: C4+re, C4re, C5re, C6+re, are effected such that steady-state operation of the overall process and of the individual process stages is assured. This improves the availability of the process, and stoppages and emergency shutdowns are avoided.

A fourteenth aspect of the invention is characterized in that the process comprises the storing of the ethylene in an ethylene storage tank, and in that the lowering of the fraction C2re and the increasing of at least one fraction selected from the group comprising: C4+re, C4re, C5re, C6+re, are effected such that the ethylene fill level in the ethylene storage tank does not go above or below a fixed value. This allows the ethylene storage tank to have smaller dimensions, and there is no need for any oversizing. This saves footprint area, energy for pressurization, and possibly refrigeration and costs.

A fifteenth aspect of the invention is characterized in that the olefin content in the olefin-containing streams of matter recycled is at least 20% by weight, preferably at least 30% by weight, most preferably at least 40% by weight. Studies show that these olefin contents are observed for different OTO processes and especially for the MTP process, and are of good suitability for the inventive rise in ethylene production.

A sixteenth aspect of the invention is characterized in that the lowering of the fraction C2re and the increasing of at least one fraction selected from the group comprising: C4+re, C4re, C5re, C6+re, are subsequently reversed in order to move the process from a second state 2 with higher ethylene production back to a first state 1 with lower ethylene production. This increases the flexibility of the process if a production campaign for production of polypropylene with a small proportion of ethylene as comonomer is to be conducted, for example in a downstream polymerization plant.

A seventeenth aspect of the invention is characterized in that the method comprises the storing of the ethylene in an ethylene storage tank, and in that the process is moved into state 1 or 2 with the condition that the ethylene fill level in the ethylene storage tank does not go above or below a fixed value. This allows the ethylene storage tank to have smaller dimensions, and there is no need for any oversizing. This saves footprint area, energy for pressurization, and possibly refrigeration and costs.

An eighteenth aspect of the invention is characterized in that the second value C2re,2 is zero, such that the ethylene-containing ethylene product stream is discharged completely from the process. This maximizes the ethylene yield, while there is only a slight change, if any, in the yield of propylene.

BRIEF DESCRIPTION OF THE DRAWING

Further features, advantages and possible applications of the invention are apparent from the following description of working and numerical examples and from the drawings. All the features described and/or depicted, on their own or in any combination, form the subject-matter of the invention, irrespective of their combination in the claims or their dependency references.

The sole FIGURE shows:

FIG. 1 is a schematic diagram of a process according to the invention.

DETAILED DESCRIPTION OF PREFERRED EMBODIMENTS

FIG. 1 shows, as a special case of an OTO process, the flow diagram of an MTP plant for performance of the invention which is initially in state 1.

The OTO reactor 100 in which the formation of olefins from oxygenates, for example methanol and/or dimethyl ether (DME), proceeds is charged via a fresh feed conduit (not shown) with oxygenates and water vapour as diluent; in addition, recycle streams are also returned to the reactor via conduits 103 and 131. Via conduit 111, the product stream from the reactor 100 is introduced into the quench system 110. A phase containing essentially water is removed from the quench system 110 via conduit 114 and introduced into a methanol recovery unit 130. The gaseous phase removed in the quench system 110 enters a compressor 120 via conduit 112. Via conduit 113, a liquid phase consisting essentially of hydrocarbons is additionally fed from the quench system 110 into the compressor 120.

From the compressor 120, a liquid stream is conducted via conduit 121 into a separation apparatus 140. In this separation apparatus 140, the C3− fraction is separated from the C4 fraction, which is why it is also referred to as depropanizer. The separation apparatus 140 is preferably configured as a separation column. The rectification in the separation apparatus 140 is preferably effected as an extractive distillation, and it is therefore possible to supply an extractant, for example methanol, via conduit 147 if desired.

The top product drawn off overhead, containing the C3− fraction, is fed via conduit 142 to a dryer 145, from which it goes on to enter a further separation apparatus 150 via conduit 146. A direct connection of separation apparatus 140 to separation apparatus 150 is also possible. In this separation apparatus 150, the C3 fraction is separated from the C2− fraction, which is why the separation apparatus 150 is also referred to as deethanizer.

Via conduit 151, the top product from the separation apparatus 150 enters a separation apparatus 160, preferably in the form of a scrubber. When it is in the form of a scrubber, a scrubbing agent, for example scrubbing water, is introduced via conduit 161 and drawn off again via conduit 162. The C2− stream present is drawn off overhead by conduit 163 and can be sent via conduit 164 to a recycle stream in conduit 103 that leads back into the reactor 100 and/or discharged from the system via conduit 165 and sent to a further separation apparatus (not shown) for purification of the products present in order to obtain, for example, ethylene present as pure product.

The bottom product from the separation apparatus 150 is fed via conduit 152 to a separation apparatus 153 that separates propane from propylene. In this so-called C3 splitter, propane is drawn off from the system via conduit 154, and this can find use as fuel gas, for example. The propylene target product is drawn off via conduit 155, and this can optionally, depending on quality demands, be sent to a further purifying apparatus 156, from which it is then discharged via conduit 157. The purification apparatus 156 may be filled, for example, with a sorbent selected for oxygenates, such that oxygenates can be removed down to small traces from the propylene product stream according to the specification.

A liquid phase is drawn off from the compressor via conduit 122, and this is sent to a separation apparatus 170 in which the C4− fraction and the oxygenates are separated from the C4+ fraction. This separation apparatus 170 is also referred to as debutanizer. Via conduit 171, the C4− fraction and the oxygenate-containing top product from the separation apparatus 170 enter the separation apparatus 140.

Via conduit 172, the bottom product from the separation apparatus 170 is introduced into a further separation apparatus 173 in which the C7+ fraction is separated from the C6 fraction, which is why the separation apparatus 173 is also referred to as dehexanizer. The bottom product is drawn off via conduit 174, 175. Via conduit 176, 177 and 178, a recycle stream can be sent to a conduit 101, which leads via conduits 102 and 103 back to the reactor 100.

Moreover, a conduit 179 may be branched off from conduit 176, and this leads into a separation apparatus 180 (gasoline stabilizer column). The gasoline obtained here is discharged as product of value via conduit 181 and conduit 175. The C4 hydrocarbons removed overhead are fed via conduit 182 to conduits 177 and 178, such that they ultimately open into the recycle stream in conduits 102, 103.

The bottom product from the separation apparatus 140 is drawn off via conduit 148 and thus enters a mixer-settler combination 190. Hydrocarbons are drawn off therefrom via conduit 191 and can be returned wholly or partly via conduits 101, 102, 103 to the reactor 100. Alternatively or additionally, it is possible to send the hydrocarbons via conduit 192 to a separation apparatus 193 which is preferably configured as an extraction. The top product from the separation apparatus 193 is discharged as fuel gas via conduit 194.

From the methanol-dimethyl ether recovery 130, an oxygenate recycle stream is firstly returned via conduit 131 to the reactor 100. Via conduits 132 and 133, it is optionally possible to feed methanol- and/or dimethyl ether-laden water into the mixer-settler unit 190, from which it can then also be fed via conduit 195 back to conduits 197 and 196.

Via conduits 132, 134, the water can be conducted as extractant into the separation apparatus 193 if it is configured as an extraction, from which it can then also be fed via conduit 197 back to conduit 196. The water can ultimately be discharged from the system via conduit 135.

According to the invention, the process is switched from a state 1 with lower ethylene production to a state 2 with higher ethylene production in that the following changes are made:

(1) The fraction C2re of the ethylene product stream which is recycled to the OTO reactor is lowered from a first value C2re,1 to a second value C2re,2, resulting in a change dC2re=C2re,1−C2re,2. In one example, the proportion C2re of the ethylene product stream is lowered to a second value C2re,2 of zero, such that the ethylene-containing ethylene product stream is discharged completely from the process.

This is implemented, for example, in the example of FIG. 1 by partial or complete closure of a dosage or barrier valve (not shown) which is present in the conduit pathway of conduit 164.

(2) The fraction C4+re of the C4+ product stream containing C4+ olefins which is recycled to the OTO reactor is lowered from a first value C4+re,1 to a second value C4+re,2, resulting in a change dC4+re=C4+re,2−C4+re,1.

This is implemented, for example, in the example of FIG. 1 by increasing the mass flow rates recycled in conduits 176 and 182 by means of metering apparatuses that are not shown in FIG. 1.

At the same time, the changes dC2re and dC4+re in a mass flow ratio dC4+re/dC2re, where the mass flow ratio is between 70% and 130%, preferably between 80% and 120%, further preferably between 90% and 110%, most preferably 100%.

In order to prevent polymerization, in one example, an inhibitor can be added to the condensers and reboilers of at least one separation column, especially the debutanizer, dehexanizer and any gasoline stabilizer column present.

The MTP process shown in FIG. 1 was at first operated in state 1. The selectivity for ethylene+ propylene was 67%, divided into 65% for propylene and 2% for ethylene.

Subsequently, the MTP process was moved interstate 2 by the inventive measures, by lowering the fraction C2re recycled to the OTO reactor to zero. The selectivity for ethylene+ propylene in state 2 was then 76%, divided into 65% for propylene and 11% ethylene.

It is thus clear that the hype propylene selectivity was not adversely affected by the inventive change. By contrast, ethylene selectivity rose by 9%. There was a proportional reduction in the mass flow rates discharged via conduits 154, 175 and 194.

The tables below are a compilation of operating data for the process according to the invention for the states of operation of "start of run" (SOR), operating time below 1000 hos, and "middle of run" (MOR), operating time above 1000 hos.

As apparent from the data compiled in the tables, in the start of the run (SOR) period of operation, at the transition from state 1 to state 2, ethylene production rises by 166 t/h, while propylene production at first falls slightly by 36 t/d.

By contrast, in the middle of run (MOR) period of operation, at the transition from state 1 to state 2, ethylene production rises by 171 t/h, while propylene production remains constant.

Since process operation in the examples was commenced with OTO catalyst previously unused for production, during the "start of run" (SOR) period of operation, the forming or conditioning of the OTO catalyst also took place, which at first leads to constant reaction characteristics of the OTO catalyst ("middle of run", MOR), before—at very long operating times in the "end of run" (EOR) operating period at typically more than 7000 hos—ageing effects occur. It was observed that the forming phase or conditioning phase was shortened when the process is moved from state 1 to state 2 at an early stage in the "start of run (SOR)" operating period. In one example, the process was moved from a first state 1 with lower ethylene production to a second state 2 with higher ethylene production after no later than 200 hours on stream. In a further example, the process was moved from a first state 1 with lower ethylene production to a second state 2 with higher ethylene production after no later than 100 hours on stream. In a further example, the process was moved from a first state 1 with lower ethylene production to a second state 2 with higher ethylene production after no later than 50 hours on stream.

TABLE 1

Operating parameters for middle of run (MOR) for 5000 t/d of methanol as feed stream, operating time more than 1000 hos (1000 to 7000 hos, averages)

| Parameter | Comp. Ex., with C2 recycle (State 1) | Invention, without C2 recycle (State 2) | Difference |
|---|---|---|---|
| Ethylene production (t/d) | 60 | 231 | 171 |
| Propylene production (t/d) | 1420 | 1420 | 0 |
| LPG production C3 + C4 + C4 = (t/d) | 110 | 67 | |
| Gasoline production C5 + (t/d) | 540 | 420 | |
| C2 paraffins (t/d) | 57 | 49 | |
| Total hydrocarbons (t/d) | 2187 | 2187 | |
| C2 recycle (t/h) conduit 164 | 26, of which: olefins: 20 paraffins: 6 | 0 | −26 −20 |
| C4 recycle (t/h) conduit 191 | 40, of which: olefins: 16.4 paraffins: 23.6 | 50 olefins: 17.8 paraffins: 32.2 | +10 +1.4 |
| C5/C6/C7 recycle (t/h), conduit 178 | 140, of which: olefins: 53.4 paraffins: 86.6 | 156 olefins: 59.3 paraffins: 96.7 | +16 +5.9 |

TABLE 1-continued

Operating parameters for middle of run (MOR) for 5000 t/d of methanol as feed stream, operating time more than 1000 hos (1000 to 7000 hos, averages)

| Parameter | Comp. Ex., with C2 recycle (State 1) | Invention, without C2 recycle (State 2) | Difference |
|---|---|---|---|
| Total olefins in the recycle (t/h) | 89.8 | 77.1 | −12.7 |
| Total recycle (t/h) conduit 103 | 206 | 206 | 0 |

TABLE 2

Operating parameters for start of run (SOR) for 5000 t/d of methanol as feed stream, operating time zero to 1000 hos (1000 hos, averages)

| Parameters | Comp. Ex., with C2 recycle (State 1) | Invention, without C2 recycle (State 2) | Difference |
|---|---|---|---|
| Ethylene production (t/d) | 60 | 226 | 166 |
| Propylene production (t/d) | 1340 | 1304 | −36 |
| LPG production C3 + C4 + C4 = (t/d) | 125 | 100 | |
| Gasoline production C5 + (t/d) | 600 | 505 | |
| C2 paraffins (t/d) | 62 | 52 | |
| Total hydrocarbons (t/d) | 2187 | 2187 | |
| C2 recycle (t/h) conduit 164 | 26, of which: olefins: 16 paraffins: 10 | 0 | −26 −16 |
| C4 recycle (t/h) conduit 191 | 40, of which: olefins: 12 paraffins: 28 | 50 olefins: 16 paraffins: 34 | +10 +4 |
| C5/C6/C7 recycle (t/h), conduit 178 | 140, of which: olefins: 45 paraffins: 95 | 156 olefins: 52 paraffins: 104 | +16 +7 |
| Total olefins in the recycle (t/h) | 73 | 68 | −5 |
| Total recycle (t/h) conduit 103 | 206 | 206 | 0 |

LIST OF REFERENCE SYMBOLS

100 OTO reactor
101-103 conduit
110 quench system
111-114 conduit
120 compressor
121-123 conduit
130 methanol-DME recovery
131-135 conduit
140 separation apparatus
142 conduit
150 separation apparatus
151, 152 conduit
153 separation apparatus
154, 155 conduit
156 purification stage
157 conduit
160 separation apparatus
161-165 conduit
170 separation apparatus
171, 172 conduit
173 separation apparatus

174-179 conduit
180 separation apparatus (gasoline stabilizer column)
181, 182 conduit
190 mixer-settler combination
191,192 conduit
193 separation apparatus
194-197 conduit
200 reactor
210 quench system
211-214 conduit
220 compressor
221-223 conduit
230 methanol-DME recovery
231-235 conduit
240 separation apparatus
242 conduit
250 separation apparatus
251, 252 conduit
253 separation apparatus
254, 255 conduit
256 purification stage
257 conduit
260 separation apparatus
261-265 conduit
270 separation apparatus
271 conduit
280 separation apparatus (gasoline stabilizer column)
281, 282 conduit
290 mixer-settler combination
291, 292 conduit
293 separation apparatus
294-297 conduit
300-306 conduit
310 evaporator
311, 312 conduit
320-323 conduit It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A process for producing olefins from oxygenates with variable production of ethylene and propylene, comprising:

(a) providing a feed stream containing oxygenates and converting the oxygenates in the feed stream under heterogeneous catalysis in an oxygenate-to-olefin reactor containing an oxygenate-to-olefin catalyst under oxygenate conversion conditions to a reactor product stream containing water, hydrocarbons and at least one oxygenate, (b) quenching the reactor product stream in at least one quench stage to obtain the following streams of matter:

(b1) a gaseous stream comprising hydrocarbons and comprising specifically olefins, (b2) a first liquid stream comprising water and oxygenates, (b3) a second liquid stream comprising hydrocarbons and comprising specifically olefins, (c) separating the gaseous stream and/or the second liquid stream in multiple stages by thermal separation methods to obtain a group of product streams, where the group of product streams comprises:

(c1) an ethylene-containing ethylene product stream which is at least partly discharged from the process, with recycling of a further fraction C2re of the ethylene product stream to the oxygenate-to-olefin reactor, (c2) a propylene-containing propylene product stream which is discharged from the process, (c3) at least one C4+ product stream containing C4+ olefins which is at least partly recycled in a fraction C4+re fraction to the oxygenate-to-olefin reactor, (c4) a gasoline product stream which comprises C4+ paraffins and aromatics and is discharged from the process, wherein (d) the process is moved from a first state 1 with lower ethylene production to a second state 2 with higher ethylene production by:

(e) lowering the fraction C2re from a first value C2re, 1 to a second value C2re,2, resulting in a change dC2re=C2re, 1-C2re,2, (f) increasing the fraction C4+re from a first value C4+re, 1 to a second value C4+re,2, resulting in a change dC4+re=C4+re,2−C4+re, 1, (g) where dC2re and dC4+re are changes in mass flow, where a mass flow ratio dC4+re/dC2re is between 70% and 130%.

2. The process according to claim 1, wherein the movement of the process from the first state 1 with lower ethylene production to the second state 2 with higher ethylene production reduces propylene production only by a maximum of 5%.

3. The process according to claim 1, wherein the process is moved from the first state 1 with lower ethylene production to the second state 2 with higher ethylene production after no earlier than 600 hours on stream of the oxygenate-to-olefin catalyst.

4. The process according to claim 1, wherein the process is moved from the first state 1 with lower ethylene production to the second state 2 with higher ethylene production after no later than 200 hours on stream of the oxygenate-to-olefin catalyst.

5. The process according to claim 1, wherein the C4+ product stream containing C4+ olefins is separated further by thermal separation methods into at least one further olefin product stream selected from the group consisting of:

(c31) a C4 olefin product stream comprising butenes which is at least partly recycled in a fraction C4re to the oxygenate-to-olefin reactor, where the recycled fraction C4re is increased from a first value C4re, 1 to a second value C4re,2, resulting in a change dC4re=C4re,2−C4re, 1, (c32) a C5 olefin product stream comprising pentenes which is at least partly recycled in a fraction C5re to the oxygenate-to-olefin reactor, where the recycled fraction C5re is increased from a first value C5re, 1 to a second value C5re,2, resulting in a change dC5re=C5re,2−C5re, 1, and (c33) a C6+ olefin product stream comprising hexenes and optionally olefins having more than six carbon atoms which is at least partly recycled in a fraction C6+re to the oxygenate-to-olefin reactor, where the recycled fraction C6+re is increased from a first value C6+re, 1 to a second value C6+re,2, resulting in a change dC6+re=C6+re,2−C6+re, 1, where the change dC4+re is calculated as the sum total of the changes dC4re+dC5re+dC6+re.

6. The process according to claim 5, wherein, from the at least one further olefin product stream, only the C4 olefin product stream is recycled at least partly in a fraction C4re to the oxygenate-to-olefin reactor.

7. The process according to claim 5, wherein, from the at least one further olefin product stream, only the C5 olefin product stream is recycled at least partly in a fraction C5re to the oxygenate-to-olefin reactor.

8. The process according to claim 5, wherein, from the at least one further olefin product stream, only the C6+ olefin product stream is recycled at least partly in a fraction C6+re to the oxygenate-to-olefin reactor.

9. The process according to claim 5, wherein, from the at least one further olefin product stream, two of these streams are recycled at least partly to the oxygenate-to-olefin reactor.

10. The process according to claim 6, wherein all other of the further olefin product streams (c31)-(c33) are recycled at least partly to the oxygenate-to-olefin reactor.

11. The process according to claim 6, wherein the lowering of the fraction C2re and the increasing of at least one fraction selected from the group consisting of: C4+re, C4re, C5re, and C6+re, are affected such that the ethylene/propylene product ratio is between 1% and 20% by weight.

12. The process according to claim 6, wherein the lowering of the fraction C2re and the increasing of at least one fraction selected from the group consisting of: C4+re, C4re, C5re, and C6+re, are affected such that steady-state operation of the overall process and of the individual process stages is assured.

13. The process according to claim 6, wherein the process comprises storing at least a portion of the ethylene product stream in an ethylene storage tank, and wherein the lowering of the fraction C2re and the increasing of at least one fraction selected from the group consisting of: C4+re, C4re, C5re, and C6+re, are affected such that an ethylene fill level in the ethylene storage tank does not go above or below a fixed value.

14. The process according to claim 1, wherein the olefin content in the olefin-containing streams of matter recycled is at least 20% by weight.

15. The process according to claim 1, wherein the lowering of the fraction C2re and the increasing of at least one fraction selected from the group comprising: C4+re, C4re, C5re, C6+re, are subsequently reversed in order to move the process from the second state 2 with higher ethylene production back to the first state 1 with lower ethylene production.

16. The process according to claim 1, wherein the method comprises storing at least a portion of the ethylene product stream in an ethylene storage tank, and wherein the process is moved into the state 1 or 2 with the condition that an ethylene fill level in the ethylene storage tank does not go above or below a fixed value.

17. The process according to claim 1, wherein the second value C2re,2 is zero, such that the ethylene-containing ethylene product stream is discharged completely from the process.

* * * * *